(12) United States Patent
West

(10) Patent No.: US 8,721,995 B2
(45) Date of Patent: May 13, 2014

(54) CONVERSION OF ORGANOSULFUR COMPOUNDS TO HYDROGEN SULFIDE IN MIXED ALCOHOL SYNTHESIS REACTOR EFFLUENT

(71) Applicant: Fluor Technologies Corporation, Aliso Viejo, CA (US)

(72) Inventor: Martin West, Huntington Beach, CA (US)

(73) Assignee: Fluor Technologies Corporation, Aliso Viejo, CA (US)

(*) Notice: Subject to any disclaimer, the term of this patent is extended or adjusted under 35 U.S.C. 154(b) by 0 days.

(21) Appl. No.: 13/667,279

(22) Filed: Nov. 2, 2012

(65) Prior Publication Data

US 2013/0116346 A1    May 9, 2013

Related U.S. Application Data

(60) Provisional application No. 61/555,063, filed on Nov. 3, 2011.

(51) Int. Cl.
| | |
|---|---|
| *B01J 8/04* | (2006.01) |
| *B01J 8/00* | (2006.01) |
| *B01J 19/00* | (2006.01) |
| *C07C 27/00* | (2006.01) |
| *C07C 27/06* | (2006.01) |

(52) U.S. Cl.
USPC ........... 422/630; 422/129; 422/187; 422/600; 518/705

(58) Field of Classification Search
USPC .................. 422/129, 187, 600, 630; 518/705
See application file for complete search history.

(56) References Cited

U.S. PATENT DOCUMENTS

| | | |
|---|---|---|
| 4,752,623 A | 6/1988 | Stevens et al. |
| 2009/0205946 A1* | 8/2009 | Reddy et al. ................. 203/75 |
| 2010/0069515 A1* | 3/2010 | Tirtowidjojo et al. ........ 518/705 |
| 2010/0264065 A1 | 10/2010 | Hamad et al. |
| 2010/0280287 A1 | 11/2010 | Kharas et al. |
| 2010/0331581 A1 | 12/2010 | Kharas et al. |
| 2011/0000823 A1 | 1/2011 | Hamad et al. |
| 2011/0201701 A1 | 8/2011 | Lucas et al. |
| 2011/0319505 A1 | 12/2011 | Janbroers et al. |

OTHER PUBLICATIONS

Li et al., Ni/ADM: a high activity and selectivity to C2+OH catalyst for catalytic conversion of synthesis gas to C1-05 mixed alcohols, Mar. 2005, Topics in Catalysis vol. 32, Nos. 3-4, 233-239.*

* cited by examiner

*Primary Examiner* — Natasha Young
(74) *Attorney, Agent, or Firm* — Fish & Tsang, LLP

(57) ABSTRACT

Plants and methods are presented in which organosulfur compounds in a mixed alcohol synthesis reactor effluent are converted into hydrogen sulfide ($H_2S$). The volatility and relative insolubility of $H_2S$ reduces the overall sulfur content of the mixed alcohol synthesis product stream while significantly reducing or even eliminating the need for process steps/equipment to remove organosulfur compounds from liquid and gaseous products.

12 Claims, 2 Drawing Sheets

CONVERSION OF ORGANOSULFUR COMPOUNDS TO HYDROGEN SULFIDE IN MIXED ALCOHOL SYNTHESIS REACTOR EFFLUENT

This application claims the benefit of priority to U.S. Provisional Application No. 61/555,063, filed Nov. 3, 2011, and incorporated by reference herein.

FIELD OF THE INVENTION

The field of the invention is devices and methods of gas treatment, particularly of effluent gas from mixed alcohol synthesis reactors.

BACKGROUND

Synthesis gas (or syngas) is a mixture of hydrogen ($H_2$) and carbon monoxide (CO) that can be obtained (in principle) from virtually any carbonaceous material, and may be utilized as a base material for the synthesis of a wide variety of commercially useful compounds, such as alcohols. Suitable carbonaceous materials for the production of syngas include both fossil resources (such as natural gas, petroleum, coal, and lignite) and renewable resources (such as lignocellulosic biomass and other carbon-rich waste materials). In many applications it may be preferable to use renewable resources for syngas production due to the rising economic and environmental impacts associated with exploitation of fossil fuel sources. There are a variety of technologies that may be used to convert such feedstocks into syngas, including steam reformation, pyrolysis, gasification, and/or partial oxidation of a carbon-containing feedstock.

Reactions similar to those of the well known Fischer-Tropsch synthesis, may be used to convert syngas into commercially useful alcohols. For example, U.S. Pat. No. 4,752,623 (to Stevens and Conway) discloses a cobalt/molybdenum/sulfur catalyst for producing mixed alcohols from syngas. Various investigators have explored formulations and manufacturing methods to improve the performance of such catalysts, as described in U.S. Patent Application No. 2010/331581 (to Kharas et al) and U.S. Patent Application No. US 2011/0319505 (to Janbroers et al). While mixed alcohol synthesis from syngas has been an area of intensive research and process development, fully developed technologies commercial technologies have not yet entered the market. This is due, at least in part, to the problem of catalyst stability and the generation of organosulfur compound contaminants during alcohol synthesis. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

In many systems and methods, mixed alcohol synthesis processes are facilitated by sulfided molybdenum catalysts. While sulfided catalysts are generally more active than their non-sulfided counterparts, reaction conditions in a mixed alcohol reactor will often lead to gradual loss of catalyst activity and the formation of various organosulfur compounds. While activity of such catalysts may be maintained by the addition of sulfur containing compounds to the syngas feed stream, as disclosed in U.S. Patent Application No. 2010/0280287 (to Kharas and May), addition of such compounds may exacerbate the problem of the formation of undesirable organosulfur compounds in the mixed alcohol synthesis reactor. These in turn appear in the reactor effluent and contaminate the mixed alcohol product stream.

Unfortunately, contaminating organosulfur compounds are often soluble in the alcohol products of such a reactor and in solvents utilized in removal of $CO_2$ or acid gas waste. U.S. Patent Application No. 2011/0201701 (to Lucas et al) discloses adsorption techniques to remove such organosulfur compounds from an ethanol product stream. Another potentially useful technology for removal of organosulfur compounds is membrane separation, as disclosed in U.S. Patent Application No. 2010/0264065 (to Hamad and Bahamdan) and U.S. Patent Application No. 2011/0000823 (to Hamad). Both of these approaches, however, introduce considerable complexity to plant operations and may not give suitably complete removal of organosulfur compounds from the alcohol products. Additionally, if not removed beforehand, a portion of the organosulfur compounds may be passed into an acid gas removal unit of an alcohol absorber or similar product separation device placed downstream from the mixed alcohol reactor (for example, by an overhead vapor collector) where they tend to interfere with the recycling and reuse of materials used for acid gas removal, thereby increasing the cost and complexity of the system.

Thus, even though various systems and methods of mixed alcohol synthesis are known in the art, there is still a need for improved systems and methods, particularly those that address reduction or removal of organosulfur compounds.

SUMMARY OF THE INVENTION

The inventive subject matter is directed towards plants, configurations, and methods in which a organosulfur products in mixed alcohol reactor effluent are converted into hydrogen sulfide ($H_2S$). Since $H_2S$ is volatile and relatively insoluble in the mixed alcohol products produced in the synthesis reactor and in the solvents utilized for acid gas removal, overall sulfur content is reduced in the mixed alcohol synthesis product streams while significantly reducing or even eliminating the need for process steps and/or equipment to remove organosulfur compounds from liquid and gaseous products. Moreover, conversion of organosulfur compounds to $H_2S$ can also reduce and potentially eliminate process steps and/or equipment for removal of organosulfur compounds from recycled gases in a mixed alcohols synthesis reactor loop.

One embodiment of the inventive concept is a method of operating a mixed alcohol synthesis plant, in which a feed gas stream is reacted in a mixed alcohol reactor to produce an effluent stream. At least part of the effluent stream is reacted in a catalytic reactor to produce a treated effluent stream, converting one or more organosulfur compound(s) into hydrogen sulfide ($H_2S$). The treated effluent stream may then be separated into an alcohol product stream and a vapor stream using an alcohol absorber. Hydrogen sulfide containing acid gas may then be removed from the vapor stream by an acid gas removal unit. Such an acid gas removal may, for example, use an amine solvent. In some embodiments of the inventive concept the alcohol product stream may be separated and purified to remove one or more organosulfur compounds from the alcohol product stream. In other embodiments of the inventive concept, efficiencies may be realized by transferring heat between the effluent stream and/or the treated effluent stream and the feed stream. Similarly, at least a portion of overhead vapor from an acid gas removal unit may be recycled to the feed gas stream.

Another embodiment of the inventive concept is a mixed alcohol synthesis plant that includes a mixed alcohol reactor that is configured to receive a feed gas stream and produce an effluent stream. The mixed alcohol synthesis plant can include a catalytic reactor that receives the effluent stream and produces a treated effluent stream. Such a catalytic reactor may be configured to convert one or more organosulfur compound(s) into hydrogen sulfide. A mixed alcohol synthesis plant of the inventive concept may include an alcohol absorber that receives the treated effluent stream and produces an alcohol product stream and a vapor stream, and an acid gas removal unit that can receive such a vapor stream and remove hydrogen sulfide containing acid gas from the vapor stream. Such an acid gas removal unit may employ an amine solvent. In some embodiments of the inventive concept the mixed alcohol synthesis plant can include a product separation and purification unit that receives the alcohol product stream and removes one or more organosulfur compound(s) from the alcohol product stream. A mixed alcohol synthesis plant of the inventive concept may realize efficiencies by, for example, including a heat exchanger that exchanges heat between the effluent stream and/or treated effluent stream and the feed gas stream. Similarly, in some embodiments of the inventive concept at least a part of the feed gas stream is recycled from the acid gas removal unit.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
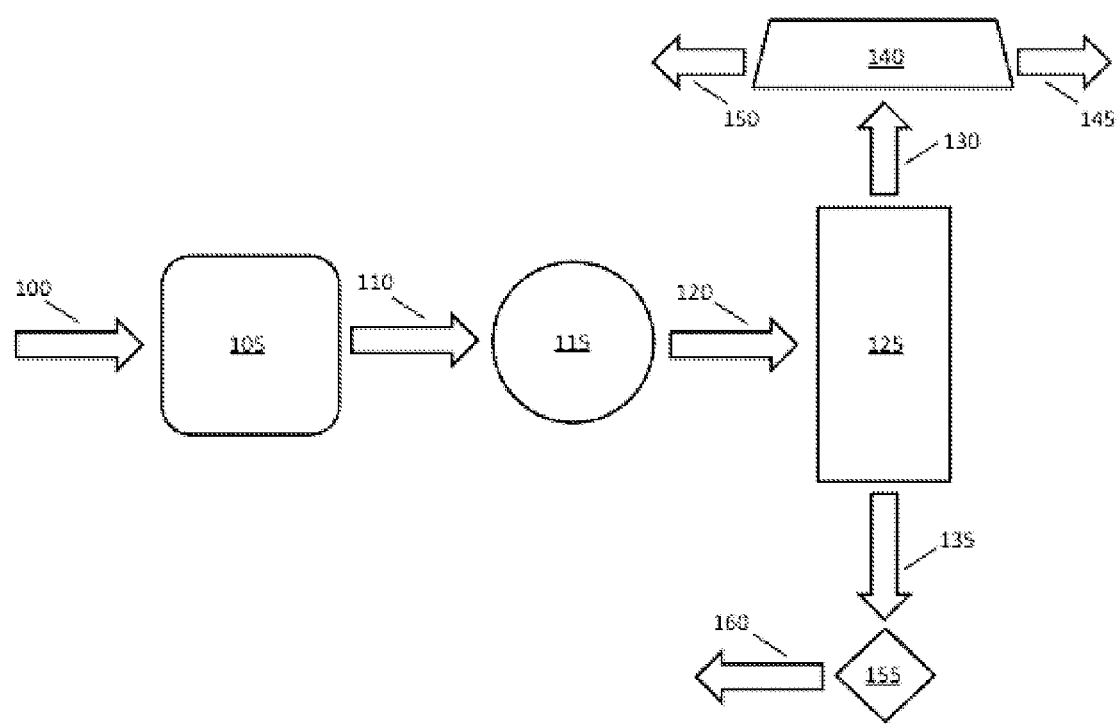
FIG. 1 is a schematic of an exemplary method according to the inventive subject matter. A catalytic reactor is downstream from a mixed alcohol reactor, converting a first organosulfur compound and/or at least a portion of organosulfur compounds in a mixed alcohol reactor effluent stream into hydrogen sulfide.

It should be noted that while the following description is drawn to methods and devices for generation of mixed alcohol products from syngas, various alternative configurations are also deemed suitable and may applied to the production of other products from syngas precursors, including formaldehyde, acetic acid, propylene, esters, plastics, and liquid fuels. One should appreciate that, in addition to sulfur-containing compounds, the inventive concept may be applied to contaminants other than sulfur and sulfur containing compounds, notably ammonia and other nitrogen containing contaminants. Such contaminants may be present in a syngas stream prior to entry into processing or may be generated during processing steps.

One should also appreciate that the disclosed techniques provide many advantageous technical effects including improved removal of organosulfur compounds from mixed alcohol products derived from syngas, and improved efficiencies in regeneration of materials utilized in acid gas removal from a mixed alcohol product stream.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The inventive subject matter is directed towards plants, configurations, and methods in which organosulfur compounds in a mixed alcohol reactor effluent are converted into hydrogen sulfide, which will not only dramatically reduce the organosulfur content of the mixed alcohol product streams, but will also significantly reduce or even eliminate the requirement for process steps/equipment to purify liquid and gaseous products. Conversion of organosulfur compounds (e.g., aliphatic and aromatic mercaptans, aliphatic and aromatic disulfides, etc.) to hydrogen sulfide will also reduce and possibly eliminate the process steps and equipment necessary to remove organosulfur compounds from recycle gas that is returned to the mixed alcohol reactor in a mixed alcohol synthesis reactor loop.

In a preferred aspect of the inventive subject matter, a mixed alcohol synthesis plant will include a mixed alcohol reactor that receives a feed gas stream and produces an effluent stream and a catalytic reactor that receives the effluent stream to produce a treated effluent stream, where the catalytic reactor includes a catalyst that is effective to convert at least a first organosulfur compound into hydrogen sulfide. In such plants an alcohol absorber then receives the so treated effluent stream to produce an alcohol product stream and a vapor stream. An acid gas removal unit receives the vapor stream and removes hydrogen sulfide containing acid gas from the vapor stream. Most typically, contemplated plants will also include a product separation and purification unit that receives the alcohol product stream and removes at least a second organosulfur compound from the alcohol product stream. It is generally preferred that the acid gas removal unit be configured to employ an amine solvent, although in alternative embodiments other solvents (such as, for example, internally generated alcohol solvents) may also be employed. Additionally, a heat exchanger may be employed to heat the feed gas stream using heat from the effluent stream and/or the treated effluent stream. In some embodiments the acid gas removal unit will provide an overhead product that can be used as a recycle gas that is directed to the mixed alcohol reactor.

One embodiment of the inventive concept is shown in FIG. 1. A feedgas 100 is supplied to a mixed alcohol reactor 105, where reactions take place convert at least a portion of the feedgas 100 into an effluent stream 110, which contains a mixture of alcohols. In a preferred embodiment, syngas may be used as a feedgas 100. Suitable syngas may be obtained from fossil fuel sources, for example from reformation of natural gas or gasification of coal. Alternatively, syngas may be obtained from partial combustion of biomass such as agricultural wastes, grasses and other cellulosic material, timber harvesting residues, softwood chips, hardwood chips, tree branches, tree stumps, leaves, bark, sawdust, off-spec paper pulp, corn stover, wheat straw, rice straw, sugarcane bagasse, switchgrass, miscanthus, grape pumice, almond shells, pecan shells, coconut shells, coffee grounds, grass pellets, hay pellets, wood pellets, cardboard, paper, plastic, cloth animal manure, municipal garbage, municipal sewage, and black liquor.

As noted above, a mixed alcohol reactor 105 may utilize a sulfided molybdenum catalyst at elevated temperatures and pressures to convert carbon monoxide and hydrogen present in the feedgas 100 into methanol, ethanol, 1-propanol, 2-propanol, 1-butanol, 2-butanol, 2-methyl-1-propanol, 2-methyl.2-propanol, and/or other $C_{5-10}$ alcohols in a process similar to Fischer-Tropsch synthesis. In practice a source of sulfur is often added to the reactor feed in order to obtain optimal catalyst performance; this may act by maintaining the molybdenum and possibly other catalyst components (for example, cobalt) in a sulfided state as is found in some hydroprocessing processes. Suitable sources of sulfur include, but are not limited to, elemental sulfur, hydrogen sulfide ($H_2S$), dimethyl sulfide, diethyl sulfide, dimethyl disulfide, dibutyl polysulfide, dioctyl polysulfide, diphenyl polysulfide, dicyclohexyl polysulfide, methylthiol, ethylthiol, cysteine, cystine, methionine, potassium disulfide, cesium disulfide, and/or sodium disulfide. Unfortunately the sulfur utilized in this process may also combine with other components in the mixed alcohol reactor 105 to form undesirable organosulfur compounds such as, for example, mercaptans, sulfides, and disulfides. It should be appreciated, however, that organosulfur compounds may derive, at least in part, from sulfur containing contaminants in the feed gas stream 100, and that such organosulfur compounds may also be treated by embodiments of the inventive concept. This advantageously permits utilization of syngas feedstocks that might otherwise be undesirable for mixed alcohol synthesis due to sulfur content. Organosulfur compounds are partly soluble in water and alcohol, and will consequently be found as contaminants not only in the effluent 110 from such a mixed alcohol reactor 105, but also in the vapor stream (such as recycle gas) originating from a downstream alcohol absorber and in solvent systems used to treat such vapor streams. This solubility greatly increases the expense and complexity of removing such organosulfur compounds.

In a preferred embodiment of the inventive concept, removal of undesired organosulfur compounds is greatly simplified and operations of plants incorporating such processes significant streamlined by the incorporating at least one catalytic reactor 115 that receives an effluent stream 110 from the mixed alcohol reactor 105, where the catalytic reactor 115 serves to convert at least a portion of the organosulfur compounds present in the effluent stream 110 into $H_2S$. The reduced vapor pressure and solubility of $H_2S$ in alcohols, water, and certain other solvents greatly simplifies removal of sulfur from this process. It should be especially appreciated that the above advantages can be implemented through the use of a (preferably highly) selective catalyst that will hydrodesulfurize the organosulfur compounds in the mixed alcohol reactor effluent 110 into $H_2S$ and hydrocarbons without substantially promoting other thermodynamically possible reactions (e.g., hydrodeoxygenation of alcohols, carboxylic acids, aldehydes and esters to water and hydrocarbons or methanation of CO and $CO_2$). For example, such use of a catalyst can be implemented in configurations similar to the use of post-treat beds of hydrotreating catalyst utilized at the bottom of hydrocracking reactors to remove olefins and/or mercaptans formed in upper levels of the reactor. Such catalysts are disclosed in U.S. Pat. No. 4,207,409 (to Ladenberger et al), U.S. Pat. No. 5,417,844 (to Boitiaux and Sarrazin), U.S. Pat. No. 5,475,173 (to Cheung and Johnson), U.S. Patent Application No. 2005/0014639 (to Bhan and Himelfarb), and U.S. Patent Application No. 2012/0043257 (to Dziabala et al). Suitable catalyst compositions may include aluminum, molybdenum, iron, cobalt, nickel, ruthenium, osmium and other class VIII metals, silver, platinum, palladium, oxygen, and/or sulfur. In some embodiments of the inventive concept the catalyst may include two metallic elements. In other embodiments of the inventive concept the catalyst may include three or more metallic elements. Catalyst compositions may also include a filler material, such as a clay. Catalysts may supplied as fixed or granular solids or, alternatively, incorporated into supports such as zeolites or as films coated onto membranes. As should be readily apparent, an appropriate choice of catalyst and operating conditions may be made in a series of experimental test runs designed so as to optimize suitable catalysts and process conditions. In a preferred embodiment of the inventive concept the catalyst should be selected to perform at temperature, pressure, and/or concentration conditions typically found between the outlet conditions of the mixed alcohol reactor 105 and the alcohol absorber 125 operations. For example, it is contemplated that (among other suitable choices) especially preferred catalysts will include commercially available low activity hydrotreating catalysts used for post-treat beds in hydrocrackers and selective hydrogenation catalysts used to hydrogenate diolefins in olefin containing streams.

As shown in FIG. 1, in some embodiments of the inventive concept a treated effluent stream 120, in which a first organosulfur compound or at least a portion of the organosulfur compounds has been converted into $H_2S$, is directed to an alcohol absorber 125. The alcohol absorber 125 separates the treated effluent stream 120 into a vapor stream 130 and an alcohol product stream 135. The vapor stream 130, which includes an $H_2S$ containing acid gas, and other volatile components, may be directed to an acid gas removal unit 140. Such an acid gas removal unit may utilize a solvent that absorbs components such as $CO_2$ and $H_2S$ in a reversible manner, thereby allowing the solvent to be regenerated. Such a solvent may, for example, absorb $CO_2$ and $H_2S$ at high pressures and/or reduced temperatures, and release $CO_2$ and $H_2S$ when temperature is increased and/or pressure is reduced. In a preferred embodiment of the inventive concept the acid gas removal unit utilizes an amine solvent such as, for example, ECONAMINE™ (Fluor Corporation, Irving, Tex. USA, 75039). In some embodiments of the inventive concept, the acid gas removal unit collects an overhead vapor and produces an $H_2S$ containing stream 145 and an acid gas stream 150. In some embodiments of the inventive concept at least a portion of the overhead vapor of the acid gas removal unit 140 can be utilized as a recycle gas and recycled to the stream of feedgas 100 (not shown). In other embodiments of the inventive concept, $H_2S$ from the $H_2S$ containing stream 145 may be treated in a sulfur processor, for example a Claus reactor, to produce elemental sulfur. In other embodiments of the inventive concept, further efficiencies may be realized by transferring heat between the effluent stream 110 and/or treated effluent stream 120 and the stream of feed gas 100, for example by using a heat exchanger.

In some embodiments of the inventive concept the alcohol product stream 135 is directed to an organosulfur removal unit 155, where a second organosulfur compound and/or residual organosulfur compounds may be removed to generate a treated alcohol product stream 160. Such an organosulfur removal unit may, for example, utilize adsorption, extraction, and/or membrane separation to remove at least a portion of the organosulfur compounds from the alcohol product stream 135.

Figure 2:
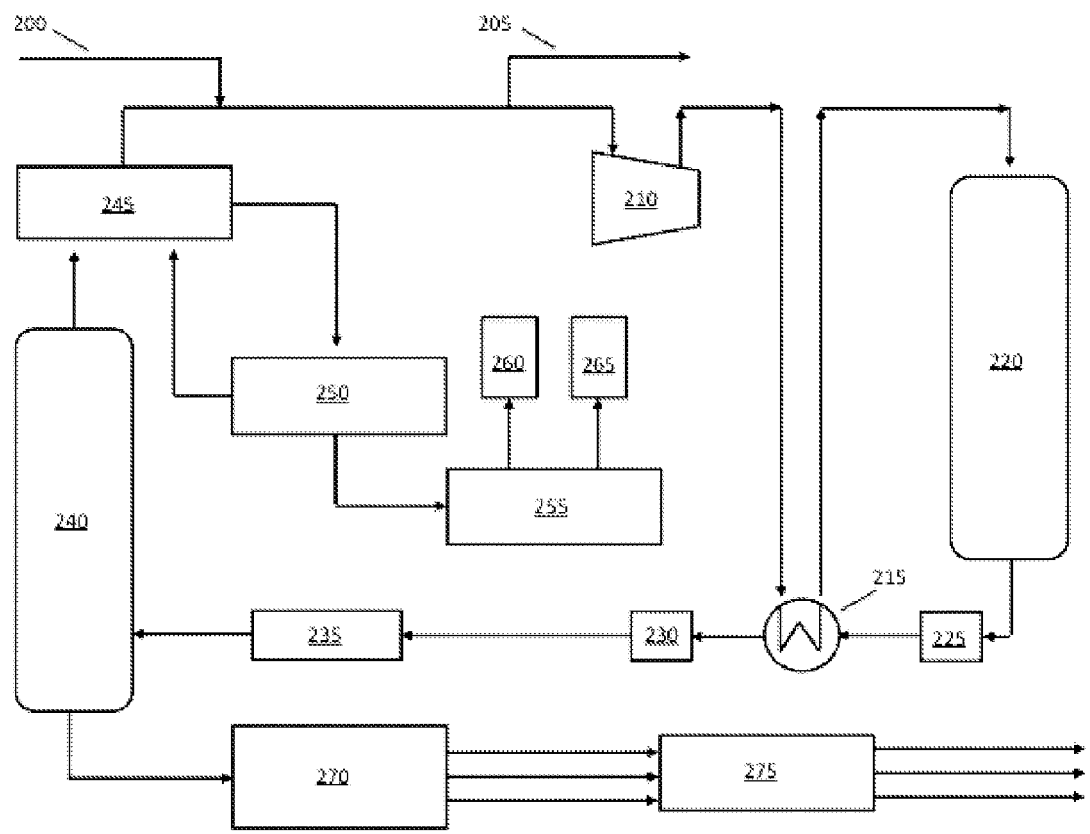
FIG. 2 is a schematic of an exemplary mixed alcohol synthesis plant according to the inventive subject matter. A catalytic reactor is downstream from a mixed alcohol reactor, converting a first organosulfur compound and/or at least a portion of organosulfur compounds present in the effluent stream into hydrogen sulfide in a catalytic reactor. The so produced hydrogen sulfide is removed by an acid gas removal unit.

Another embodiment of the inventive concept is shown in FIG. 2, which illustrates an exemplary schematic for a plant according to the inventive subject matter. As shown, a feed gas stream 200 (for example, syngas) is directed to a compressor 210, which may be used to optimize the pressure of the feed gas stream as it is directed to a mixed alcohol reactor 220. In some embodiments of the inventive concept a bleed line 205 may be utilized to direct at least a portion of the feed gas stream 200 elsewhere, permitting optimization of plant operations. For example, if feed gas is available in excess of the needs of mixed alcohol synthesis a portion of the feed gas stream 200 may be directed via a bleed line 205 to a burner that supplies heat for plant processes and/or a turbine that supplies power that is utilized by the plant. As noted above, the mixed alcohol reactor 220 can employ a sulfided molybdenum catalyst or other suitable catalyst to treat syngas at elevated temperatures and pressures to convert carbon monoxide and hydrogen into an effluent stream that includes mixed alcohols such as, for example, methanol, ethanol, propanol and butanol in a process similar to Fischer-Tropsch synthesis. It should be noted that plant efficiencies may be realized by transferring heat from this effluent stream to the feed gas stream, for example through the use of a heat exchanger 215. Sulfur, for example in the form of hydrogen sulfide, may be included in the reactor feed to optimize catalyst performance. Such sulfur may act by maintaining the molybdenum (and possibly other catalyst components) in a sulfided state, as is true with some hydroprocessing processes. Unfortunately, sulfur necessary for the process can also combine in the mixed alcohol reactor 220 with other components to form organosulfur compounds, such as mercaptans, sulfides, and disulfides, removal of which is notoriously difficult and/or costly. These organosulfur byproducts are partially soluble in water and alcohol, and will consequently become contaminants in not only the effluent stream of the mixed alcohol reactor 220, but also in the gases originating from downstream processing units, such as alcohol absorbers, and in components of downstream acid gas removal units.

To facilitate removal of organosulfur compounds from an effluent stream produced by a mixed alcohol reactor 220, such an effluent stream may be directed to one or both of catalytic reactors 225, 230. Such catalytic reactor 225, 230 may be utilized to convert a first organosulfur compound and/or a portion of the organic sulfur compounds in the mixed alcohol reactor 220 effluent into $H_2S$, thereby producing a treated effluent stream with reduced organosulfur content. It should be noted that plant efficiencies may be realized by transferring heat from this treated effluent stream to the feed gas stream, for example through the use of a heat exchanger 215. In some embodiments of the inventive concept a heat exchanger may be utilized to transfer heat from the mixed alcohol reactor 220 effluent to the feed gas stream. It should be particularly appreciated that the catalytic reactor 225, 230 may be positioned in both or one of two positions (upstream or downstream from the heat exchanger 215), indicated as 225 and 230. It should be especially appreciated that a catalytic reactor 225, 230 may utilize a (preferably highly) selective catalyst that will hydrodesulfurize the organosulfur compounds in the mixed alcohol reactor 220 effluent into $H_2S$ and hydrocarbons without substantially promoting other thermodynamically favorable reactions (e.g., hydrodeoxygenation of alcohols, carboxylic acids, aldehydes and esters to water and hydrocarbons or methanation of CO and $CO_2$). Suitable catalysts are disclosed in U.S. Pat. No. 4,207,409 (to Ladenberger et al), U.S. Pat. No. 5,417,844 (to Boitiaux and Sarrazin), U.S. Pat. No. 5,475,173 (to Cheung and Johnson), U.S. Patent Application No. 2005/0014639 (to Bhan and Himelfarb), and U.S. Patent Application No. 2012/0043257 (to Dziabala et al). Suitable catalyst compositions may include aluminum, molybdenum, iron, cobalt, nickel, ruthenium, osmium and other class VIII metals, silver, platinum, palladium, oxygen, sulfur, and/or combinations thereof. Catalyst compositions may also include a filler material, such as a clay. Catalysts may supplied as fixed or granular solids or, alternatively, incorporated into supports such zeolites or as films coated onto membranes. As should be readily apparent, an appropriate choice of catalyst and operating conditions may be made in a series of experimental test runs designed so as to optimize suitable catalysts and process conditions. In a preferred embodiment of the inventive concept the catalyst should be selected to perform at temperature, pressure, and/or concentration conditions typically found between the outlet of the mixed alcohol reactor 220 and downstream alcohol absorber. It is still further contemplated that (among other suitable choices) especially preferred catalysts will include commercially available low activity hydrotreating catalysts used for post-treat beds in hydrocrackers and selective hydrogenation catalysts used to hydrogenate diolefins in olefin containing streams.

Following treatment in a catalytic reactor 225, 230 to reduce the concentration of organosulfur compounds the treated effluent is directed to an alcohol absorber 240, which separates the treated effluent to produce a vapor stream. In some embodiments of the inventive concept, the treated effluent is passed through a cooler 235 before reaching the alcohol absorber 240. At least a portion of the vapor stream produced in the alcohol absorber 240 is $H_2S$ containing acid gas, which contains at least a portion of the $H_2S$ produced in the catalytic reactor 225, 230. This vapor stream is directed to an acid gas removal unit 245. In some embodiments of the inventive concept the acid gas removal unit 245 may utilize a solvent to absorb $H_2S$ and other contaminants and/or byproducts (such as $CO_2$) from the vapor stream. A portion of the overhead vapor from such an acid gas removal unit 245 may be directed to join the feed gas stream 200 as recycle gas. In a preferred embodiment of the inventive concept the solvent utilized in the acid gas removal unit 245 is selected so that $H_2S$ and other contaminants/byproducts are reversibly soluble, for example being soluble in the solvent at low temperatures and/or elevated pressures and released from the solvent at high temperatures and/or reduced pressures. Suitable solvents are physical and chemical solvents, and especially include an amine solvent (which may or may not be selective towards H2S). Solvents utilized in the acid gas removal unit 245 may be regenerated in order to realize plant efficiency, for example by being circulated through a loop that incorporates a solvent regenerator 250. Acid gas released from the solvent in the solvent regenerator 250 may be directed to an acid gas treatment unit 255, which can produce $H_2S$ 260 and vent 265 streams. It should be noted that $H_2S$ recovered in such a manner may be oxidized to elemental sulfur, which may be disposed of without release into the atmosphere or may utilized for commercial purposes.

The alcohol absorber 240 produces an alcohol product stream that is directed to a product purification and separation unit 270. Such a product purification and separation unit 270 may, for example, separate alcohol products into two or more oxygenate product streams containing different alcohols and/or other oxygenates produced in the mixed alcohol reactor 220. In some embodiments of the inventive concept, a second organosulfur compound or at least a portion of residual organosulfur contaminants in the oxygenate product streams may be removed by treatment in an organosulfur removal unit 275 to produce treated oxygenate product streams. Such an organosulfur removal unit may 275, for example, utilize adsorption, extraction, and/or membrane separation technologies. In other embodiments of the inventive concept the alcohol product stream from the alcohol absorber 240 may be treated by an organosulfur removal unit prior to separation into oxygenate product streams.

With respect to the source of syngas it should be noted that all known sources are contemplated, and that the choice of source will depend primarily on source material availability and other economic and/or regulatory factors. For example, suitable source materials/processes for providing the syngas include coal steam gasification or natural gas reformation, gasification of renewable organic matter, biomass, etc. As a consequence of this additional process steps may be required to achieve a desirable ratio of $H_2$ to CO in syngas so as to provide suitable conditions for the efficient production of mixed alcohols. Consequently, and depending on the quantity of recycle gas, the product composition of the mixed alcohol synthesis may also vary.

Regardless of the particular composition and catalyst used, it should be recognized that the hydrodesulfurization of the organosulfur compounds in the mixed alcohol reactor effluent is preferably performed under conditions that reduce, suppress, or even eliminate undesired side reactions. Thus, the specific operating conditions and types of catalyst will vary considerably. For example, hydrodesulfurization of the organosulfur compounds is performed using a catalyst and under conditions such that at least 70%, more typically at least 80%, and more typically at least 90% of all organosulfur compounds in the effluent stream are converted into H2S and the corresponding hydrocarbon product. Similarly, it is preferred that under hydrodesulfurization conditions less than 20%, more preferably less than 10%, and most preferably les than 5% of oxygenate compounds are hydrodeoxygenated. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

It should be appreciated that, with respect to the mixed alcohol reactor and/or the catalytic reactor, a wide variety of reactor designs may be suitable. Embodiments of the inventive concept may include a variety of configurations using a fixed bed reactor and/or a fluidized bed reactor. In some embodiments of inventive concept a radial flow reactor or reactors may be employed. In mixed alcohol reactors and/or catalytic reactors of the inventive process the reaction zone may be housed in a single vessel; in other embodiments the reaction zone may be housed in a series of vessels. In preferred embodiments of the inventive concept, the catalyst of the mixed alcohol reactor and/or the catalytic reactor is employed in a fixed bed reactor, for example, in the shape of a pipe or tube, where the reactants, typically in the vapor form, are passed over or through the catalyst. Other reactors, such as fluid or ebullient bed reactors, may be employed, however. In some embodiments of the inventive concept inert materials may be utilized in conjunction with the catalysts of the mixed alcohol reactor and/or the catalytic reactor in order to optimize the pressure change in the reactant stream across the catalyst bed and/or optimize the contact time of the reactants with the catalyst.

With respect to the acid gas removal unit, it should be noted that all such known units are suitable, and especially include those that use a chemical solvent (and particularly an amine solvent) such as, for example, the ECONAMINE™ system (Fluor Corporation, Irving, Tex. USA, 75039). However, as alternative and less preferred embodiments of the inventive concept physical solvents are expressly not excluded. For example, a portion of the mixed alcohol product may be utilized as a $CO_2$ removal solvent (although this might require significant cooling). Similarly, the particular nature and type of product separation and purification is not critical to the inventive subject matter, and it should be noted that all conventional devices and methods are contemplated herein.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A mixed alcohol synthesis plant, comprising:
    a mixed alcohol reactor configured to receive a feed gas stream and to produce an effluent stream;
    a catalytic reactor configured to receive the effluent stream and produce a treated effluent stream, wherein the catalytic reactor is configured to convert a first organo sulfur compound in the effluent stream into hydrogen sulfide and a hydrocarbon;
    an alcohol absorber configured to receive the treated effluent stream and to produce an alcohol product stream and a vapor stream; and
    an acid gas removal unit that is configured to receive the vapor stream and to remove the hydrogen sulfide from the vapor stream.

2. The mixed alcohol synthesis plant of claim 1 further comprising a product separation and purification unit that is configured to receive the alcohol product stream and to remove at least a second organosulfur compound from the alcohol product stream.

3. The mixed alcohol synthesis plant of claim 1 wherein the acid gas removal unit is configured to employ an amine solvent.

4. The mixed alcohol synthesis plant of claim 1 further comprising a heat exchanger that exchanges heat between the effluent stream or treated effluent stream and the feed gas stream.

5. The mixed alcohol synthesis plant of claim 1 wherein at least a portion of the feed gas stream is recycled from the acid gas removal unit.

6. The mixed alcohol synthesis plant of claim 1, wherein the catalytic reactor comprises a catalyst, and wherein the catalyst comprises a group VIII metal.

7. A method of operating a mixed alcohol synthesis plant, comprising:
    reacting in a mixed alcohol reactor a feed gas stream to produce an effluent stream;

reacting at least part of the effluent stream in a catalytic reactor to produce a treated effluent stream, wherein the step of reacting comprises converting a first organosulfur compound in the effluent stream into hydrogen sulfide and a hydrocarbon;

separating in an alcohol absorber the treated effluent stream into an alcohol product stream and a vapor stream; and removing in an acid gas removal unit the hydrogen sulfide from the vapor stream.

8. The method of claim 7 further comprising a step of separating and purifying the alcohol product stream to thereby remove at least a second organosulfur compound from the alcohol product stream.

9. The method of claim 7 wherein the acid gas removal unit uses an amine solvent.

10. The method of claim 7 further comprising a step of using a heat exchanger to exchange heat between the effluent stream or treated effluent stream and the feed gas stream.

11. The method of claim 7 further comprising a step of recycling at least a portion of an overhead vapor from the acid gas removal unit acid to the feed gas stream.

12. The method of claim 7, wherein the catalytic reactor comprises a catalyst, and wherein the catalyst comprises a group VIII metal.

* * * * *